US006974671B1

(12) United States Patent
Montminy et al.

(10) Patent No.: US 6,974,671 B1
(45) Date of Patent: Dec. 13, 2005

(54) METHODS FOR INDENTIFYING COMPOUNDS THAT MODULATE GLUCONEOGENESIS THROUGH THE BINDING OF CREB TO THE PGC-1 PROMOTER

(75) Inventors: Marc R. Montminy, San Diego, CA (US); Bruce M. Spiegelman, Waban, MA (US); Stephan Herzig, Del Mar, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 10/244,045

(22) Filed: Sep. 11, 2002
(Under 37 CFR 1.47)

Related U.S. Application Data (60) Provisional application No. 60/323,141, filed on Sep. 12, 2001.

(51) Int. Cl.$^7$ .................. C12Q 1/68; G01N 33/00; C07H 19/00; C07H 21/00; C07H 21/02
(52) U.S. Cl. .................. 435/6; 435/94; 435/325; 435/455; 536/23.1; 536/23.5; 536/24.1; 514/44; 424/93.1; 800/21; 204/450
(58) Field of Search .................. 536/23.1, 23.5, 536/24.1; 514/44; 424/93.1; 435/325, 455, 435/6; 800/21; 436/94; 204/450

(56) References Cited

U.S. PATENT DOCUMENTS

| | | | |
|---|---|---|---|
| 4,683,195 A | 7/1987 | Mullis et al. .................. 435/6 |
| 4,683,202 A | 7/1987 | Mullis .................. 435/91.2 |
| 4,800,159 A | 1/1989 | Mullis et al. .................. 435/91.2 |
| 5,082,830 A | 1/1992 | Brakel et al. .................. 435/6 |
| 5,143,854 A | 9/1992 | Pirrung et al. .................. 436/518 |
| 5,242,974 A | 9/1993 | Holmes .................. 525/54.11 |
| 5,288,514 A | 2/1994 | Ellman .................. 435/4 |
| 5,312,233 A | 5/1994 | Tanny et al. .................. 417/316 |
| 5,384,261 A | 1/1995 | Winkler et al. .................. 436/518 |
| 5,405,783 A | 4/1995 | Pirrung et al. .................. 436/518 |
| 5,412,087 A | 5/1995 | McGall et al. .................. 536/24.3 |
| 5,424,186 A | 6/1995 | Fodor et al. .................. 435/6 |
| 5,429,807 A | 7/1995 | Matson et al. .................. 422/121 |
| 5,436,327 A | 7/1995 | Southern et al. .................. 536/25.34 |
| 5,445,934 A | 8/1995 | Fodor et al. .................. 435/6 |
| 5,472,672 A | 12/1995 | Brennan .................. 422/131 |
| 5,527,681 A | 6/1996 | Holmes .................. 435/6 |
| 5,529,756 A | 6/1996 | Brennan .................. 422/131 |
| 5,532,128 A | 7/1996 | Eggers et al. .................. 435/6 |
| 5,545,531 A | 8/1996 | Rava et al. .................. 435/6 |
| 5,554,501 A | 9/1996 | Coassin et al. .................. 435/6 |
| 5,556,752 A | 9/1996 | Lockhart et al. .................. 435/6 |
| 5,561,071 A | 10/1996 | Hollenberg et al. .................. 438/503 |
| 5,571,639 A | 11/1996 | Hubbell et al. .................. 430/5 |
| 5,593,839 A | 1/1997 | Hubbell et al. .................. 435/6 |
| 5,599,695 A | 2/1997 | Pease et al. .................. 435/91.1 |
| 5,624,711 A | 4/1997 | Sundberg et al. .................. 427/261 |
| 5,658,734 A | 8/1997 | Brock et al. .................. 435/6 |
| 5,677,195 A | 10/1997 | Winkler et al. .................. 436/518 |
| 5,700,637 A | 12/1997 | Southern .................. 435/6 |
| 5,945,526 A | 8/1999 | Lee et al. .................. 536/26.6 |
| 6,004,755 A | 12/1999 | Wang .................. 435/6 |
| 6,017,696 A | 1/2000 | Heller .................. 435/6 |
| 6,024,138 A | 2/2000 | Fritz et al. .................. 141/31 |
| 6,051,380 A | 4/2000 | Sosnowski et al. .................. 435/6 |
| 6,110,426 A | 8/2000 | Shalon et al. .................. 422/68.1 |
| 6,129,828 A | 10/2000 | Sheldon, III et al. .................. 204/518 |

FOREIGN PATENT DOCUMENTS

WO    WO 97/27317    7/1997

OTHER PUBLICATIONS

Vidal-Puig, et al. (2001) Nature, 413: 125-26.*
Yoon, et al. (2001) Nature, 413: 131-38.*
Herzig, et al. (2001) Nature, 413: 179-83.*
Herzig, et al. (2001) Nature, 413: 652.*
Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Ahn et al., "A dominant-negative inhibitor of CREB reveals that it is a general mediator stimulus-dependent transcription of c-fos." Molec. Cell. Biol., 18(2): 967-977 (1998).
Becker et al., "Use of recombinant adenovirus for metabolic engineering of mammalian cells." Methods Cell Biol, 43: 161-189 (1994).
Brown & Botstein, "Exploring the new world of the genome with DNA microarrays," Nature Genetics Supp., 21:33-37, 1999.
Chalifour et al., "A method for analysis of gene expression patterns," Anal. Biochem, 216: 299-304, 1994.

(Continued)

*Primary Examiner*—Dave Trong Nguyen
*Assistant Examiner*—Robert M. Kelly
(74) *Attorney, Agent, or Firm*—Foley & Lardner; Stephen E. Reiter (57) ABSTRACT

In accordance with the present invention, it has been discovered that CREB regulates hepatic gluconeogenesis via the co-activator, PGC-1. PGC-1 potentiated glucocorticoid induction of the gene for PEPCK, the rate limiting enzyme in gluconeogenesis, via the glucocorticoid response unit in the promoter, indicating that activation of PGC-1 by CREB in liver contributes to the pathogenesis of diabetes mellitus. In accordance with the above discoveries, the present invention provides a method of identifying a compound that modulates gluconeogenesis. The invention method comprises contacting CREB and a nucleic acid comprising a PGC-1 promoter with a test compound, and determining if the test compound modulates binding between CREB and the PGC-1 promoter.

3 Claims, 4 Drawing Sheets

OTHER PUBLICATIONS

Chen et al., "Evidence that the diabetes gene encodes the leptin receptor: identification of a mutation in the leptin receptor gene in db/db mice." Cell, 84:491-495, 1996.

Cheung et al, "Making and reading microarrays," Nature Genetics Supp., 21:15-19, 1999.

Consoli, A., "Role of liver in pathophysiology of NIDDM." Diabetes Care, 15:430-441, 1992.

Cook et al., "Segregation analysis of NIDDM in Caucasian families." Diabetologia, 37:1231-1240, 1994.

DeFronzo, R.A., "The Triumvirate: β-Cell, muscle, liver, a collusion responsible for NIDDM." Diabetes, 37:667-687, 1988.

Fire et al., "Potent and specific genetic interference by double-stranded RNA in *Caenorhabditis elegans*." Nature, 391:806-811, 1998.

Friedman et al., "Phosphoenolpyruvate carboxykinase (GTP) gene transcription and hyperglycemia are regulated by glucocorticoids in genetically obese db/db transgenic mice." J. Biol Chem, 272: 31475-31481, 1997.

Gonzalez, G. & Montminy, M., "Cyclic AMP stimulates somatostatin gene transcription by phosphorylation of CREB at Serine 133." Cell, 59:675-680, 1989.

Harris et al., "Onset of NIDDM occurs at least 4-7 Yr before clinical diagnosis." Diabetes Care, 15:815-819, 1992.

He et al., "A simplified system for generating recombinant adenoviruses." Proc. Natl. Acad. Sci., 95:2509-2514, 1998.

Hong et al., "Sequencing of large double-stranded DNA using the dideoxy sequencing technique." Bioscience Reports, 2: 907-912, 1982.

Houghten et al., "Generation and use of synthetic peptide combinatorial libraries for basic research and drug discovery." Nature, 354:84-86, 1991.

Imai et al., "Characterization of a complex glucocorticoid response unit in the phosphoenolpyruvate carboxykinase gene." Mol Cell Biol, 10: 4712-4719, 1990.

Jitrapakdee et al., "The rat pyruvate carboxylase gene structure: Alternate promoters generate multiple transcripts with the 5'-end heterogeneity." J Biol Chem, 272: 20522-20530, 1997.

Ju et al., "Design and synthesis of fluorescence energy transfer dye-labeled primers and their application for DNA sequencing and analysis." Anal. Biochem. 231(1):131-140, 1995.

Ju et al., "Fluorescence energy transfer dye-labeled primers for DNA sequencing and analysis." Proc. Nat. Acad. Sci. (USA) 92:4347-4351, 1995.

Kennerdell and Carthew, "Use of dsRNA-mediated genetic interference to demonstrate that *frizzled* and *frizzled* 2 act in the wingless pathway." .Cell, 95:1017-1026, 1998.

King et al., "Global socioeconomic development trends (1985-1988)." Wld. Health Statistical Quarterly, 42:190-196, 1989.

Knutti et al., "A tissue-specific coactivator of steroid receptors, identified in a functional genetic screen." Mol Cell Biol, 20:2411-2422, 2000.

Kobberling, J., "Studies on the genetic heterogeneity of diabetes mellitus." Diabetologia 7:46-49, 1971.

Lam et al., "A new type of synthetic peptide library for identifying ligand-binding activity." Nature, 354:82-84, 1991.

Lee et al., "Abnormal splicing of the leptin receptor in *diabetic* mice," Nature, 379: 632-635, 1996.

Lei et al., "Glucose-6-phosphatase dependent substrate transport in the glycogen storage disease type-1a mouse." Nat Genet, 13: 203-209, 1996.

Lipshutz et al., "High density synthetic oligonucleotide arrays." Nature Genetics Supp., 21:20-24, 1999.

Liu et al., "The mouse albumin promoter and a distal upstream site are simultaneously DNase I hypersensitive in liver chromatin and bind similar liver-abudant factors in vitro." Genes Dev, 2: 528-541, 1988.

Liu et al., "Cyclic AMP induction of phosphoenolpyruvate carboxykinase (GTP) gene transcription is mediated by multiple promoter elements." J Biol Chem, 266:19095-19102, 1991.

Long et al., "The CREB family of activators is required for endochondral bone development." Development 128:541-550, 2001.

McGraw, R., "Dideoxy DNA sequencing with end-labeled oligonucleotide primers," Anal. Biochem., 143: 298-303, 1984.

Michael et al., "The phosphorylation status of a cyclic AMP-responsive activator is modulated via a chromatin-dependent mechanism." Mol Cell Biol., 20:1596-1603, 2000.

Nakajima et al., "RNA Helicase A mediates association of CBP with RNA polymerase II." Cell, 90:1107-1112, 1997.

Newman et al., "Concordance for Type 2 (non-insulin-dependent) diabetes mellitus in male twins." Diabetologia 30:763-768, 1987.

Pietu et al., "Novel gene transcripts preferentially expressed in human muscles revealed by quantitative hybridization of high density cDNA array." Genome Res., 6:492-503, 1996.

Puigserver et al., "A cold-inducible coactivator of nuclear receptors linked to adaptive thermogenesis." Cell, 92; 829-839, 1998.

Quinn, P. G. & Granner, D. K., "Cyclic AMP-dependent protein kinase regulates transcription of the phosphoenolpyruvate carboxykinase gene but not bining of nuclear factors to the cyclic AMP regulatory element." Mol Cell Biol, 10:3357-3364, 1990.

Raval, J., "Qualitative and quantitative determination of mRNA." Pharmacol. Toxicol Methods, 32:125-127, 1994.

Rudolph et al., "Impaired fetal T cell development and perinatal lethality in mice lacking the cAMP response element binding protein." Proc Natl Acad Sci U S A, 95:4481-4486, 1998.

Saiki et al., "Primer-directed enzymatic amplification of DNA with a thermostable DNA polymerase." Science, 239: 487-491, 1988.

Schena et al., "Parallel human genome analysis: Microarray-based expression monitoring of 1000 genes." P.N.A.S. U.S. A., 93:10614-10616, 1996.

Schena et al., "Quantitative monitoring of gene expression patterns with a complementary DNA microarray." Science, 270:467-470, 1995.

Schmoll et al., "Identification of a cAMP response element within the glucose-6-phosphatase hydrolytic subunit gene promoter which is involved in the transcriptional regulation by cAMP and glucocorticoids in H4IIE hepatoma cells." Biochem J, 338: 457-463, 1999.

Shoemaker et al., "Experimental annotation of the human genome using microarray technology." Nature, 409:922-927, 2001.

Short et al., "Characterization of the phosphoenolpyruvate carboxykinase (GTP) promoter-regulatory region. II. Identification of cAMP and glucocorticoid regulatory domains." J Biol Chem, 261:9721-9726, 1986.

Soares, M.B., "Identification and cloning of differentially expresssed genes." Curr. Opin. Biotechnol., 8:542-546, 1997.

Songyang et al., "SH2 domains recognize specific phosphopeptide sequences." Cell, 72:767-778, 1993.

Stolz & Tuan, "Hybridization of biotinylated Oligo(dT) for eukaryotic mRNA quantitation." Mol. Biotechnol., 6: 225-230, 1986.

Tyagi and Kramer, "Molecular beacons: probes that fluoresce upon hybridization." Nat. Biotechnol., 14:303-308. 1996.

Wang et al., "The phosphoenolpyruvate carboxykinase gene glucocorticoid response unit; identification of the functional domains of accessory factors HNF3 beta (hepatic nuclear factor-3 beta) and HNF4 and the necessity of proper alignment of their cognate binding sites." Mol Endocrinol., 13;604-618, 1999.

Wexler et al., "Molecular characterization of pyruvate carboxylase deficiency in two consanguineous families," Pediatr Res., 43:579-584, 1998.

Zhao et al., "High density cDNA filter analysis; a novel approach for large-scale, quantitative analysis of gene expression," Gene, 156:207-213, 1995.

* cited by examiner

METHODS FOR INDENTIFYING COMPOUNDS THAT MODULATE GLUCONEOGENESIS THROUGH THE BINDING OF CREB TO THE PGC-1 PROMOTER

ACKNOWLEDGMENT

This invention was made in part with Government support under Grant No. GM 37828 provided by the National Institutes of Health. The Government may have certain rights in this invention.

FIELD OF THE INVENTION

The present invention relates to methods of therapy and to analytical detection methods. In a particular aspect, the present invention relates to methods for treating diabetes mellitus using compounds that inhibit PGC-1 expression or activity. In another aspect, the invention relates to diagnosing predisposition to diabetes mellitus by determining the expression level of PGC-1 protein or mRNA.

BACKGROUND OF THE INVENTION

Many eukaryotic genes are regulated in an inducible, cell type-specific fashion. Genes expressed in response to heat shock, steroid/thyroid hormones, phorbol esters, cyclic adenosine monophosphate (cAMP), growth factors and heavy metal ions are examples of this class. The activity of cells is controlled by external signals that stimulate or inhibit intracellular events. The process by which an external signal is transmitted into and within a cell to elicit an intracellular response is referred to as signal transduction. Signal transduction is generally initiated by the interaction of extracellular factors (or inducer molecules, i.e., growth factors, hormones, adhesion molecules, neurotransmitters, and other mitogens) with receptors at the cell surface. Extracellular signals are transduced to the inner face of the cell membrane, where the cytoplasmic domains of receptor molecules contact intracellular targets. The initial receptor-target interactions stimulate a cascade of additional molecular interactions involving multiple intracellular pathways that disseminate the signal throughout the cell.

Many of the proteins involved in signal transduction contain multiple domains. Some of these domains have enzymatic activity and some of these domains are capable of binding to other cellular proteins, DNA regulatory elements, calcium, nucleotides, lipid mediators, and the like.

Protein—protein interactions are involved in all stages of the intracellular signal transduction process—at the cell membrane, where the signal is initiated in the cytoplasm by receptor recruitment of other cellular proteins, in the cytoplasm where the signals are disseminated to different cellular locations, and in the nucleus where proteins involved in transcriptional control congregate to turn on or turn off gene expression.

Mitogenic signaling affects the transcriptional activation of specific sets of genes and the inactivation of others. The nuclear effectors of gene activation are transcription factors that bind to DNA as homomeric or heteromeric dimers. Phosphorylation also modulates the function of transcription factors, as well. Oncogenes, first identified as the acute transforming genes transduced by retroviruses, are a group of dominantly acting genes. Such genes, which are involved in cell division, encode growth factors and their receptors, as well as second messengers and mitogenic nuclear proteins activated by growth factors.

The binding of growth factors to their respective receptors activates a cascade of intracellular pathways that regulate phospholipid metabolism, arachidonate metabolism, protein phosphorylation, calcium mobilization and transport, and transcriptional regulation. Specific phosphorylation events mediated by protein kinases and phosphatases modulate the activity of a variety of transcription factors within the cell. These signaling events can induce changes in cell shape, mobility, and adhesiveness, or stimulate DNA synthesis. Aberrations in these signal-induced events are associated with a variety of hyperproliferative diseases ranging from cancer to psoriasis.

The ability to repress intracellular signal-induced response pathways is an important mechanism in negative control of gene expression. Selective disruption of such pathways would allow the development of therapeutic agents capable of treating a variety of disease states related to improper activation and/or expression of specific transcription factors. For example, in patients with non-insulin dependent diabetes mellitus (NIDDM), hyperglycemia develops, in part as a result of β cell failure secondary to chronic insulin resistance. This hyperglycemia appears to be exacerbated by hyperglucogonemia and increased hepatic gluconeogenesis. cAMP appears to be the major starvation state signal which triggers glucagon gene expression as well as transcription of PEPCK, the rate limiting enzyme in gluconeogenesis.

Hyperglycemia is associated with an increased risk for all of the common late complications of diabetes mellitus, which are the major causes of morbidity and mortality in diabetics. However, there is no generally applicable and consistently effective means of maintaining plasma glucose fluctuations within a normal range in diabetics, and efforts to do so entail significant risks of causing frequent or severe hypoglycemic episodes. Nevertheless, common treatments include diet management and the use of insulin preparations and oral hypoglycemic agents.

Diabetes mellitus is among the most common of all metabolic disorders, affecting up to 11% of the population by age 70. Type I diabetes (insulin dependent diabetes mellitus or IDDM) represents about 5 to 10% of this group and is the result of a progressive autoimmune destruction of the pancreatic beta-cells with subsequent insulin deficiency.

There are two classes of type II diabetes (non-insulin dependent diabetes mellitus or NIDDM). One typically presents in older people; thus it is sometimes called mature onset diabetes. Another form, though similar to mature onset, presents in a subject at a very early age. Type II diabetes represents 90–95% of the affected population, more than 100 million people worldwide (King, H. and Zimmer, P. (1988) Wld Hlth. Statist. Quart. 41:190–196; Harris, M. I., et al. (1992) Diabetes Care 15:815–819), and is associated with peripheral insulin resistance, elevated hepatic glucose production, and inappropriate insulin secretion (DeFronzo, R. A. (1988) Diabetes 37:667–687). Family studies point to a major genetic component (Newman, B. et al. (1987) Diabetologia 30:763–768; Kobberling, J. (1971) Diabetologia 7:46–49; Cook, J. T. E. (1994) Diabetologia 37:1231–1240). However, few susceptibility genes have been identified.

Type II diabetes is characterized by a patient's inability to respond to insulin and/or insufficient insulin secretion. Insulin exerts a dominant effect on the regulation of glucose homeostasis. In the liver, insulin inhibits the production of glucose by inhibiting gluconeogenesis and glycogenolysis. Insulin is thought to act by causing cells to absorb glucose from the blood stream. Once absorbed, the liver converts glucose to glycogen. The liver supplies glucose by converting glycogen stores to glucose. Insulin also has a major role in the regulation of protein and lipid metabolism through a variety of actions that affect the flux of protein and lipid substrates.

The glucolytic pathway is central in the understanding of the lack of glucose homeostasis in diabetes. There is very tight cellular control of glycolysis. This control is achieved by the regulatory inhibition by certain glycolytic enzymes depending on the level of various glucose degradation products. Since the degradation products of glucose are also important precursors or intermediates in other aspects of metabolism, the regulatory enzymes in carbohydrate catabolism also recognize and respond to appropriate signals from other metabolic pathways.

Some of the enzymes involved in the degradation of glucose are known to be regulated and/or contain binding sites for HNF1 and/or HNF4. The first step in the degradation of glucose is the phosphorylation of glucose to glucose-6-phosphate and is carried out by an enzyme called glucokinase. The hormone insulin, secreted by the pancreas into the blood whenever the blood glucose concentration is high, stimulates the synthesis of glucokinase. In the diabetic condition, which is characterized by a defect in insulin secretion and/or amount of insulin, glucokinase is typically also deficient.

In addition to regulation of the rate of glycolysis through control of the entry of free glucose, the sequence of reactions from glucose to pyruvate is also under biological control. The enzyme that converts phosphoenol pyruvate to pyruvate and ATP is called pyruvate kinase. At high ATP concentrations the affinity of pyruvate kinase for phosphoenol pyruvate is relatively low. Pyruvate kinase is also inhibited by acetyl-CoA and by long chain fatty acids. Therefore, whenever ample fuels are available for respiration, glycolysis is inhibited by the action of pyruvate kinase. Since glucokinase contains HNF1 binding sites at its promoter region and pyruvate kinase contains HNF4 binding sites, modulation of the bioactivity of glucokinase and/or pyruvate kinase can be an effective therapy for type II diabetes.

As mentioned above, insulin has a role in lipid metabolism. Diabetes is associated with lipid related disorders such as obesity, elevated cholesterol and triglycerides. When there is an excess of glucose in the blood, the liver produces lipids instead of glucose. High levels of circulating insulin causes the liver to increase the production of lipids. Therefore, metabolism of lipids and carbohydrates is intimately related.

There remains, therefore, a need in the art for methods to selectively disrupt intracellular signal-induced response pathways. In addition, there remains a need in the art for more effective methods for the treatment of diabetes and for detecting predisposed individuals so as to provide pre-emptive therapy early in the disease or to detect early stage disease so as to reduce morbidity.

SUMMARY OF THE INVENTION

In accordance with one aspect of the present invention, it has been discovered that in the fasted state, glucose homeostasis is achieved by triggering expression of gluconeogenic genes in response to glucagon and glucocorticoids. Both pathways act synergistically to induce gluconeogenesis, although the underlying mechanism has not been determined. Here it is shown that mice deficient in CREB, secondary to targeted disruption of the CREB gene or to over-expression of a dominant negative inhibitor, exhibit fasting hypoglycemia and reduced expression of gluconeogenic enzymes. CREB was found to induce expression of the gluconeogenic program via the nuclear receptor co-activator PGC-1, which is a direct target for CREB regulation. Indeed, over-expression of PGC-1 in CREB deficient mice restored glucose homeostasis and rescued expression of gluconeogenic genes. In transient assays, PGC-1 potentiated glucocorticoid induction of the gene for PEPCK, the rate limiting enzyme in gluconeogenesis, via a glucocorticoid response unit in the promoter. These results reveal that PGC-1 promotes cooperativity between cAMP and glucocorticoid signaling pathways on hepatic gluconeogenesis. As fasting hyperglycemia is strongly correlated with type II diabetes, the results presented herein establish that the activation of PGC-1 by CREB in liver contributes importantly to the pathogenesis of this disease. In related work[1], PGC-1 is shown to be induced in diabetic animals and to increase gluconeogenic enzyme expression in cultured hepatocytes.

In accordance with the above discoveries, the present invention provides a method of treating diabetes mellitus by administering compounds that inhibit the ability of PGC-1 to induce expression of genes encoding enzymes of the gluconeogenic pathway. In another aspect, the present invention provides an assay for determining if an individual is predisposed or has early stage diabetes mellitus, the assay comprising detecting the level of expression of PGC-1 or its encoding mRNA in samples from the individual.

These and other embodiments of the present invention are described in detail below.

BRIEF DESCRIPTION OF THE FIGURES

FIG. 1 collectively demonstrates that transgenic mice expressing a dominant negative CREB inhibitor in liver display profound hypoglycemia at birth. FIG. 1A, Bottom, presents Western blot of liver nuclear extracts from wild-type (lane 1) and A-CREB transgenic (lane 2) mice using anti-CREB antiserum 244.

FIG. 2 collectively demonstrates that CREB activity is required for glucose homeostasis during fasting.

FIG. 3A presents results of a transient assay of HepG2 cells transfected with PGC-1 luciferase reporter (−170 to +68) and treated with forskolin (10 $\mu$M), A-CREB expression vector, or insulin. PGC-1 promoter CRE element shown.

FIG. 4 collectively demonstrates that PGC-1 mediates induction of the PEPCK gene via the glucocorticoid response unit (GRU). Transient assay of HepG2 hepatoma cells transfected with PEPCK luciferase reporter vectors either (FIG. 4A) containing (−490) or (FIG. 4B) lacking (−355) the GRU. Treatment with forskolin (10 μM) and/or dexamethasone ($10^{-7}$ M) indicated. Effect of PGC-1 and A-CREB vectors on PEPCK promoter activity shown. Averages±SEM shown. CREB stimulates PEPCK promoter activity directly via a consensus CRE and indirectly via induction of PGC-1, which induces the GRU via interaction with glucocorticoid receptor.

DETAILED DESCRIPTION OF THE INVENTION

Cyclic AMP (cAMP) regulates the transcription of numerous genes through protein kinase-A (PK-A) mediated phosphorylation, at Ser133, of transcription factor CREB. Binding of CREB to the nuclear CREB Binding Protein (CBP) is necessary for cAMP regulated transcription.

Figure 1A:
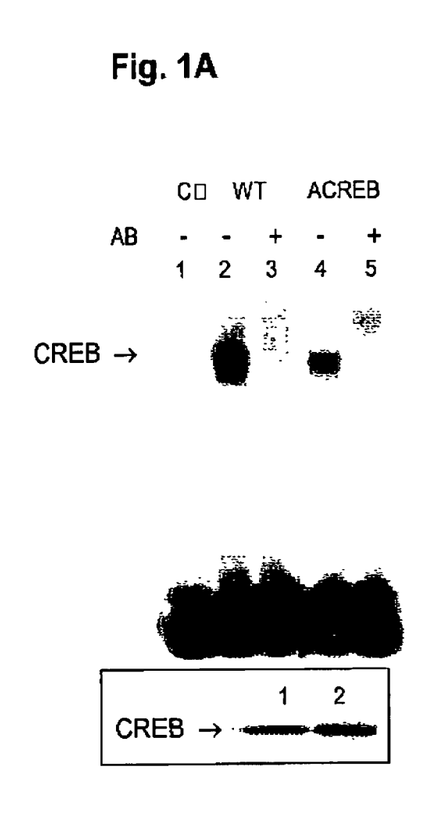
FIG. 1A, top, presents a gel mobility shift assay of newborn liver nuclear extracts from A-CREB transgenic mice and wild-type littermates using $^{32}$P-labeled CRE oligonucleotide.
Figure 1B:
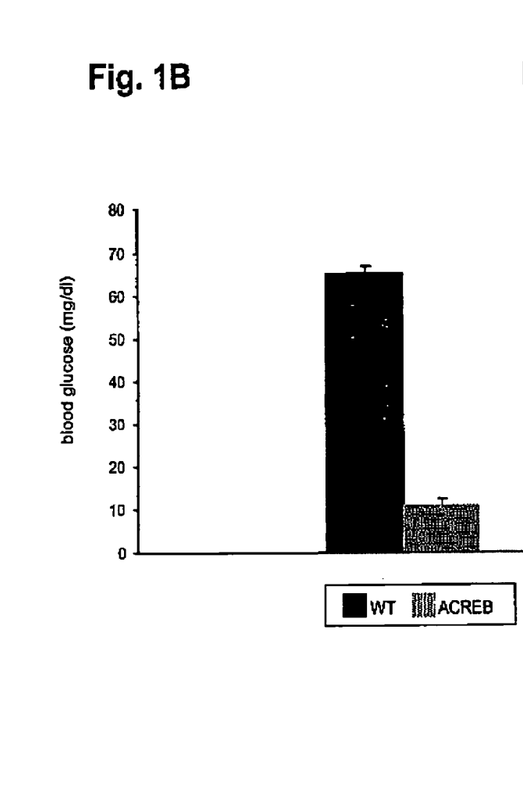
FIG. 1B presents blood glucose measurements of A-CREB transgenic and wild-type littermates at birth prior to feeding. Averages±SEM (n=5 per group)
Figure 1C:
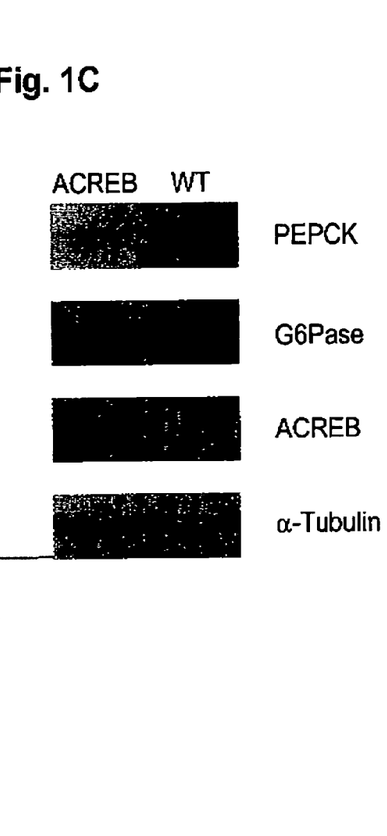
FIG. 1C presents Northern blot analysis of PEPCK, glucose 6 phosphatase (G6Pase), A-CREB, and tubulin RNAs in livers from wild-type and A-CREB transgenic mice.

CREB stimulates the gluconeogenic PEPCK gene.[3,4] The effect of CREB on the gluconeogenic pathway in transgenic mice which express a dominant negative CREB protein, referred to as A-CREB, under control of the liver specific albumin promoter/enhancer was then evaluated[5]. A-CREB contains the leucine zipper of CREB plus an acidic extension that enhances the affinity for and disrupts the DNA binding activity of CREB family members (CREB, CREM, ATF-1) but not other bZIP proteins[6,7]. CREB CRE binding activity was reduced 80% in liver nuclear extracts from A-CREB transgenic mice compared to wild-type littermates by gel mobility shift assay (FIG. 1A, compare lanes 2 and 4), despite comparable levels of full length CREB protein by Western blot assay (FIG. 1A, bottom). A-CREB mice were profoundly hypoglycemic (FIG. 1B); and RNA levels for the gluconeogenic enzymes PEPCK and glucose 6-phosphatase (G6Pase) in liver were reduced in these animals compared to wild-type littermates (FIG. 1C).

Figure 2A:
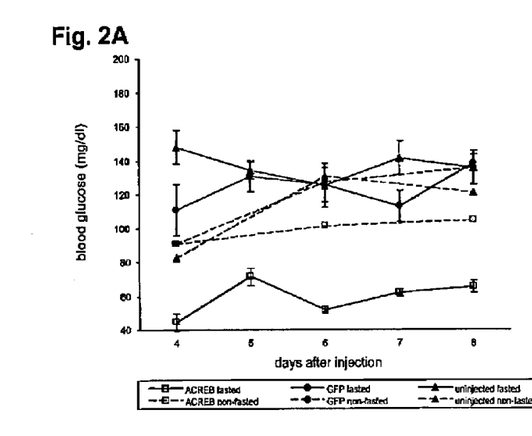
FIG. 2A presents blood glucose levels in 6 week old male mice (n=6 per group) injected with control (GFP) adenovirus, A-CREB adenovirus, or left uninjected, under fed or fasted (9 hours) conditions as indicated.
Figure 2B:
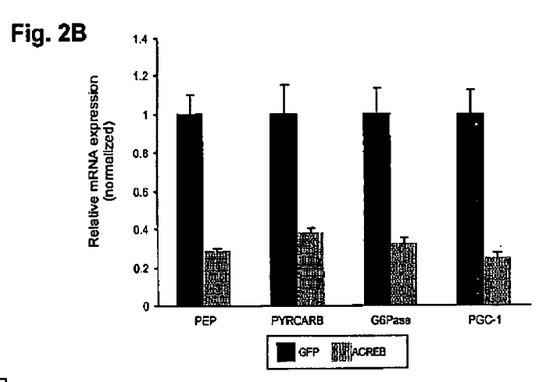
FIG. 2B presents fasting RNA levels for PEPCK, G6Pase, and pyruvate carboxylase (PC) in livers (n=3 per group) from control (GFP) and A-CREB adenovirus infected mice.

To evaluate acute effects of CREB activity on glucose homeostasis, an adenovirus expressing A-CREB under control of the CMV promoter was prepared. Following systemic injection of either A-CREB or control adenovirus, 80–90% of hepatocytes in livers of 6 week old male mice were infected as determined by visualizing fluorescence from a co-expressed green fluorescent protein (GFP) marker (not shown). In the fed state, blood glucose levels in A-CREB infected mice were comparable to mice infected with control virus (FIG. 2A; 104±10 mg/dl vs. 135±20 mg/dl at day 8, respectively). During the fasting period, however, glucose levels were far lower in A-CREB compared to control injected mice (65±4 mg/dl vs. 138±5 mg/dl at day 8, respectively), demonstrating that CREB activity is required to mobilize glucose via the gluconeogenic pathway (FIG. 2A). Indeed, expression of the PEPCK, G6Pase, and pyruvate carboxylase (PC) genes was reduced 5-fold in livers of A-CREB compared to control mice (FIG. 2B). Blood insulin levels in control and A-CREB mice were comparable under both fed and fasted states, arguing against potential effects of A-CREB on insulin secretion or clearance.

Figure 2C:
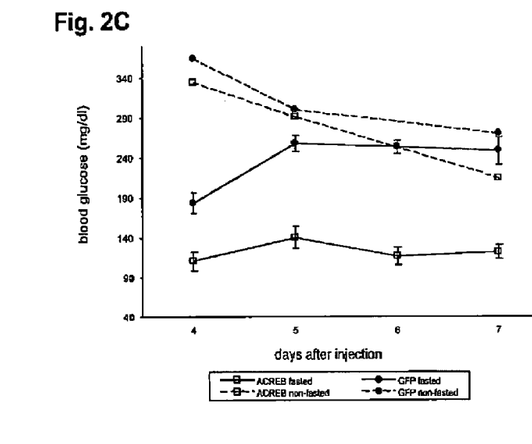
FIG. 2C presents blood glucose levels in db/db diabetic mice infected with control (GFP) and A-CREB viruses as above.
Figure 2D:
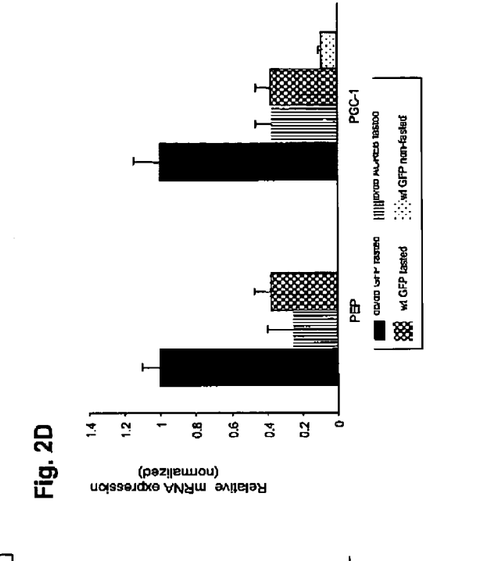
FIG. 2D presents PEPCK and PGC-1 mRNA levels in fed and fasted mice. Injection of control (GFP) and A-CREB viruses indicated. Averages±SEM.

Fasting hyperglycemia is strongly correlated with insulin resistance in type II diabetic patients[8]. To test the role of CREB in hepatic glucose production in this setting, db/db diabetic mice, which display adult onset diabetes due to a mutation in the leptin receptor gene[9,10] were employed. Compared to wild-type mice, blood glucose levels in db/db mice were significantly elevated both in the fed and fasted states (FIG. 2C; 270±17 mg/dl (fed) and 250±16 mg/dl (fasted) at day 7). Coincident with this elevation, PEPCK mRNA levels were 2.5 fold higher in fasted db/db relative to wild-type mice (FIG. 2D, compare bars 1 and 3). Following injection with A-CREB virus, fasted db/db mice became normoglycemic (FIG. 2C, 122±9 mg/dl at day 7) and PEPCK RNA levels returned to normal (FIG. 2D, bar 2).

The reduced expression of G6Pase and PC genes in A-CREB expressing mice is consistent the hypoglycemic effects of A-CREB during fasting; disruption of either gene leads to severe hypoglycemia[11,12]. Remarkably, the G6Pase promoter lacks a discernable CRE[13] and the PC gene contains only a weak CRE half-site[14], suggesting an indirect role for CREB in the regulation of both genes. In related work (see reference 1), expression of the nuclear receptor co-activator PGC-1 is shown to be induced in diabetes and to stimulate gluconeogenic enzymes in cultured hepatocytes[1], suggesting the potential value of examining the role of PGC-1 in mediating CREB signaling under fasting conditions in vivo.

Figure 3:
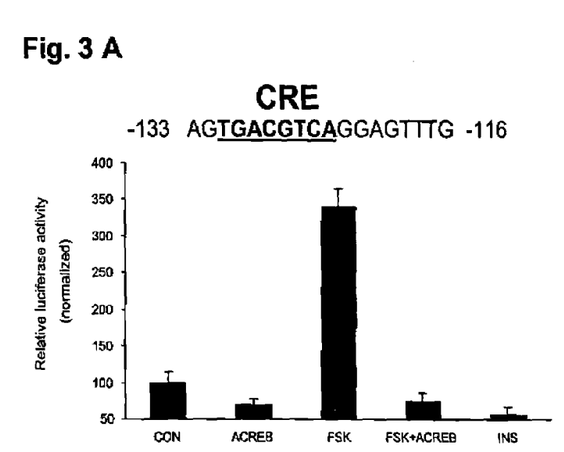
FIG. 3 collectively illustrates that PGC-1 promotes hepatic gluconeogenesis via CREB during fasting.

PGC-1 RNA levels in normal adult liver were elevated 4-fold after 8 hours of food restriction (FIG. 2D, compare bars 6 and 7); and expression of A-CREB blocked PGC-1 induction (FIG. 2B). Consistent with the fasting hyperglycemia in db/db mice, PGC-1 RNA levels were induced 3-fold in db/db compared to wild-type mice (FIG. 2D, compare bars 4 and 6); over-expression of A-CREB reduced PGC-1 RNA levels to normal (FIG. 2D, bar 5). Supporting the notion that PGC-1 is a direct target for CREB, sequence analysis of the mouse PGC-1 promoter revealed a full palindromic consensus CRE centered at −130 (FIG. 3A). In transient assays of HepG2 hepatoma cells, PGC-1 promoter activity was induced 3–4 fold by cAMP agonist (FIG. 3A). Co-transfection of an A-CREB expression vector blocked induction of the PGC-1 promoter by cAMP, demonstrating that PGC-1 is indeed a direct target for CREB activity in hepatocytes (FIG. 3A). Consistent with down-regulation of PGC-1 under feeding conditions, PGC-1 reporter activity was blocked in cells treated with insulin (10 nM, FIG. 3A).

Figure 3B:
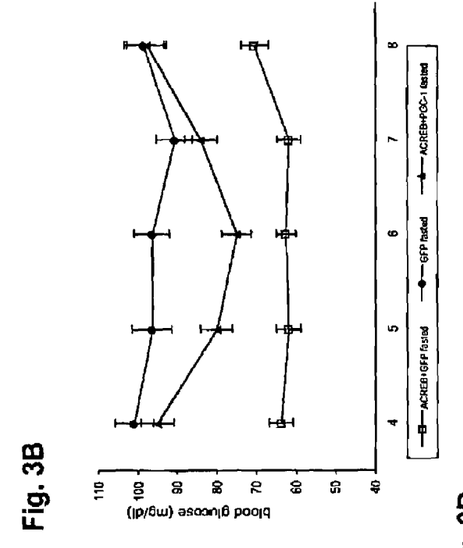
FIG. 3B presents fasting glucose levels of mice injected with GFP, A-CREB+GFP, or A-CREB+PGC-1 adenoviruses. Time course shown.
Figure 3C:
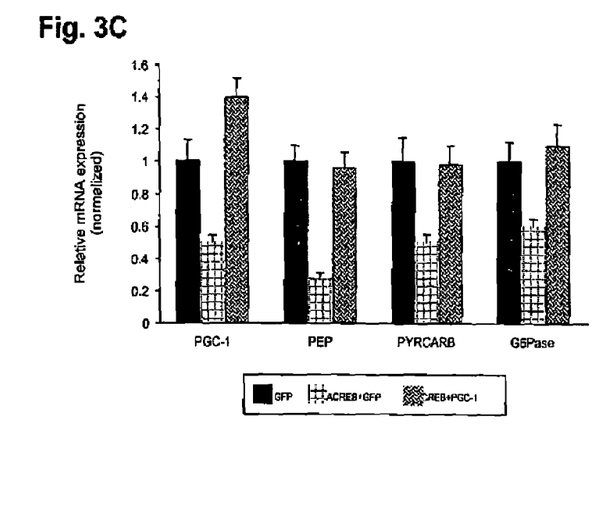
FIG. 3C presents fasting liver RNA levels of PGC-1, PEPCK, PC, and G6Pase following 8 day infection with above viruses.

The ability of cAMP to induce a nuclear receptor co-activator in liver suggested the possibility that PGC-1 promotes cooperativity between cAMP and glucocorticoid pathways during fasting. Towards this end, mice were co-infected with A-CREB and PGC-1 adenovirus constructs (FIG. 3B). A-CREB adenovirus alone induced hypoglycemia in fasted mice and inhibited expression of gluconeogenic and PGC-1 genes (FIGS. 3B and 3C). Co-infection with PGC-1 adenovirus restored fasting glucose levels to near normal and rescued gluconeogenic gene expression in A-CREB mice (FIGS. 3B and 3C). Arguing against a non-specific effect of PGC-1 on A-CREB expression, levels of the A-CREB inhibitor protein were identical in mice injected with A-CREB plus PGC-1 viruses compared to A-CREB alone.

Figure 3D:
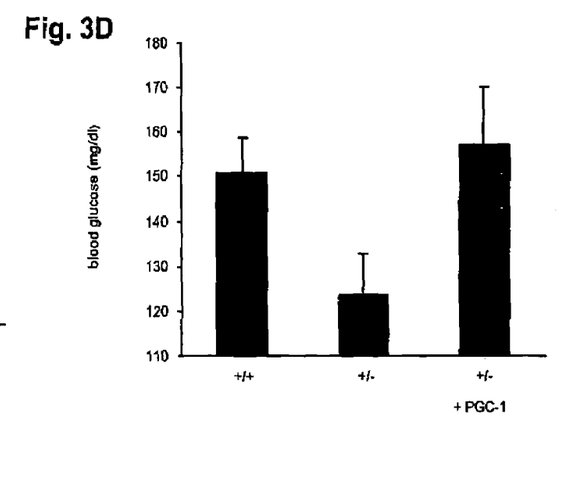
FIG. 3D presents fasting glucose levels in CREB+/− and wild type littermates infected with GFP or PGC-1 virus for 8 days. Averages±SEM shown.

To test further the importance of PGC-1 in promoting hepatic gluconeogenesis via CREB, CREB+/−mice[15] were employed. CREB+/−heterozygotes had lower fasting blood glucose levels compared to wild-type littermates (FIG. 3D); and injection of PGC-1 adenovirus corrected the relative glucose imbalance in fasted CREB+/−mice, revealing the ability of this co-activator to act downstream of CREB to promote hepatic gluconeogenesis (FIG. 3D).

Figure 4A:
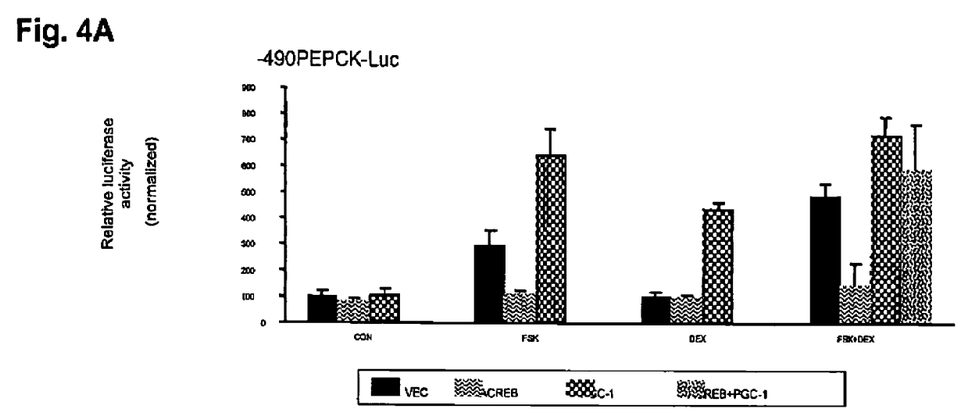
Figure 4B:
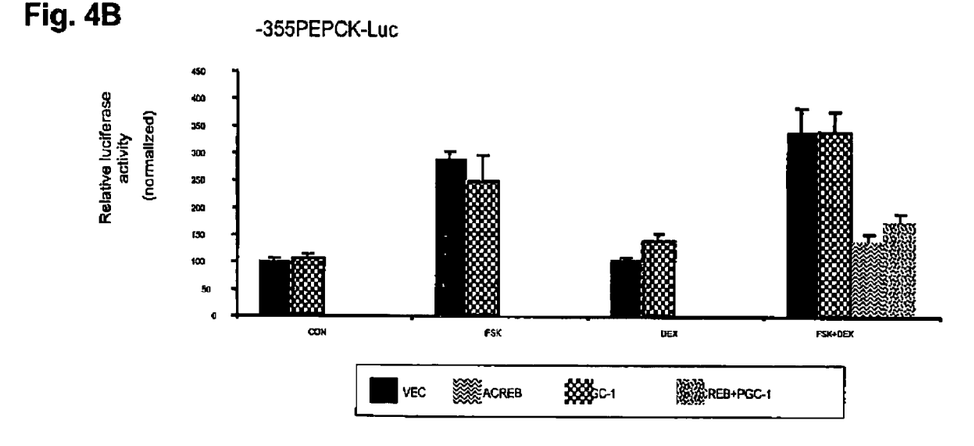

To determine the mechanism by which PGC-1 regulates expression of gluconeogenic genes, transient assays of HepG2 cells were performed using a PEPCK reporter plasmid. Treatment with cAMP agonist stimulated PEPCK promoter activity 3–4 fold (FIG. 4A); and, consistent with the presence of a consensus CRE sequence in the PEPCK promoter[16], co-transfection of A-CREB inhibitor plasmid blocked reporter induction (FIG. 4A). Over-expression of PGC-1 potentiated cAMP-dependent induction of a −490 PEPCK promoter construct in HepG2 cells, but had no effect on a −355 PEPCK reporter lacking the glucocorticoid response unit (GRU: −455 to −340) (FIG. 4B). The GRU consists of binding sites for glucocorticoid receptor plus additional transcription factors such as HNF4 and HNF3[17] that collectively mediate induction of the PEPCK promoter in response to glucocorticoids and insulin resistance[18,19].

The ability of PGC-1 to interact with and potentiate the activity of the glucocorticoid receptor[20] suggested the potential value of examining the effect of PGC-1 on induction of the PEPCK promoter by glucocorticoids. Dexamethasone treatment or PGC-1 over-expression alone had little effect on PEPCK promoter activity in HepG2 cells (FIG. 4A); but co-transfection of PGC-1 expression vector strongly induced −490 PEPCK promoter activity in response to dexamethasone (FIG. 4A). Supporting a GRU dependent mechanism of activation, PGC-1 had no effect on a PEPCK reporter construct lacking the GRU (−355 PEPCK) in cells treated either with dexamethasone or cAMP agonist (FIG. 4B).

Taken together, the results presented herein argue for a two step model in the activation of gluconeogenic genes by CREB during fasting. Ser133 phosphorylation of CREB in response to catecholamine and glucagon stimulation during the early fasting period induces certain gluconeogenic enzymes (PEPCK) via a direct CREB mediated effect. Under prolonged fasting, CREB further potentiates gluconeogenic genes (PEPCK, PC, and G6Pase) by inducing expression of the co-activator PGC-1 in liver. PGC-1 then mediates activation of the gluconeogenic program in response to glucocorticoid signals. This model is consistent with the observation that the GRU in the PEPCK gene is abnormally activated in type II diabetes, and that treatment with glucocorticoid antagonist reduces blood glucose levels in db/db diabetic mice[19].

The effect of A-CREB on liver gene expression is remarkably specific. The absence of significant inhibitory effects on other metabolic pathways suggests that CREB is an ideal target for therapeutic intervention. Although use of a dominant negative inhibitor such as A-CREB may not be feasible in this regard, small molecules that block CREB phosphorylation or disrupt recruitment of the CREB co-activator CBP are expected to be effective. Such compounds may be particularly beneficial as adjunctive therapy in lowering fasting blood glucose levels in type II diabetics.

Application to Diabetes Mellitus

In view of the above discoveries, the present invention provides a method of treating diabetes mellitus by administering to an individual afflicted with diabetes mellitus an effective amount of a compound that inhibits the ability of PGC-1 to induce expression of genes encoding enzymes of the gluconeogenic pathway. The method is preferably applied to those individuals who exhibit increased PGC-1 protein activity or increased levels of expression of PGC-1 protein mRNA. Methods to detect the activity of PGC-1 or levels of mRNA are described further below.

In one embodiment, the candidate inhibitor compound has the capacity to inhibit the level of expression of PGC-1 in cells of the individual. In other embodiments, the PGC-1 expression inhibitory compounds include those that inhibit the activity of PGC-1, reduce the level of translation from PGC-1 mRNA or reduce the level of PGC-1 encoding mRNA. In the latter case, a reduced level of expression of PGC-1 encoding mRNA can be achieved by a compound that inhibits transcription of PGC-1 mRNA or that increases the turnover rate of such mRNA. A variety of drug screening assays useful for identifying suitable candidate compounds for treating diabetes mellitus are described.

In another embodiment, an individual with diabetes mellitus can be treated by administering an effective amount of a dominant negative mutant of PGC-1 or an expression vector that encodes a dominant negative mutant of PGC-1, wherein administration of said vector results in expression of the dominant negative mutant in the individual. Dominant negative mutants of PGC-1 are characterized by having a changed amino acid sequence relative to the wildtype form of the protein wherein the change results in a loss of function. The dominant negative mutant also has the ability to prevent proper functioning of the wildtype form of the protein. Dominant negative mutants of PGC-1 can be identified in screening assays by testing a library of PGC-1 mutants for loss of biological activity (e.g., loss of the ability to induce expression of gluconeogenic enzymes) and for the ability to inhibit activity of wildtype PGC-1. Assays suitable for this purpose are described elsewhere herein.

In yet another embodiment, an individual with diabetes mellitus can be treated by administering an effective amount of an anti-sense nucleic acid for PGC-1. Useful anti-sense compounds for PGC-1 have been described in U.S. Pat. No. 6,166,192 to Spiegelman et al. Antisense oligomers of about 15 nucleotides are preferred, since they are easily synthesized and are more likely than larger oligonucleotides to be introduced into the target cell.

In still yet another embodiment, an individual with diabetes mellitus can be treated by administering an effective amount of a double stranded RNAi for PGC-1. RNAi (RNA interference) is an anti-sense RNA which when introduced as a homologous double stranded RNA (dsRNA) specifically targets a gene's product, resulting in null or hypomorphic phenotypes. The use of double stranded RNA sequences for inhibiting gene expression is well known (see Kennerdell et al., Cell 95:1017–1026 (1998); Fire et al., Nature 391:806–811 (1998)).

Drug Screening Assays:

The above described compounds can be identified by appropriate drug screening assays, which can be achieved using methods and materials already known in the art. Drug screening assays useful herein typically include screening a candidate/test compound or agent for the ability to interact with (e.g., bind to) PGC-1 protein and/or to modulate PGC-1 activity, to modulate the interaction of PGC-1 protein and a target molecule, or to modulate PGC-1 nucleic acid expression. The assays may use isolated PGC-1 protein or PGC-1 nucleic acid or cells expressing PGC-1. Candidate/test compounds include, for example, 1) peptides such as soluble peptides, including Ig-tailed fusion peptides and members of random peptide libraries (see, e.g., Lam, K. S. et al. (1991) Nature 354:82–84; Houghten, R. et al. (1991) Nature 354:84–86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) proteins including mutants of PGC-1; 5) nucleic acid compounds such as anti-sense nucleic acids; 6) double stranded RNA including double stranded RNA encoding PGC-1; 7) small organic and inorganic molecules (e.g., molecules obtained from combinatorial and natural product libraries), and the like.

Compounds that bind to PGC-1 can be screened in cell-free assays which include combining PGC-1 protein or a biologically active portion thereof, and a candidate/test compound, e.g., under conditions which allow for interaction of (e.g., binding of) the candidate/test compound to the PGC-1 protein or portion thereof to form a complex, and detecting the formation of a complex, in which the ability of the candidate compound to interact with (e.g., bind to) the PGC-1 polypeptide or fragment thereof is indicated by the presence of the candidate compound in the complex. Formation of complexes between the PGC-1 protein and the candidate compound can be quantitated, for example, using standard immunoassays.

Drug screening assays also are useful to identify candidate/test compounds which modulate (e.g., stimulate or inhibit) the interaction between PGC-1 and a molecule (target molecule) with which the PGC-1 protein normally interacts. Examples of such target molecules include the regulatory or promoter regions of genes encoding gluconeogenic enzymes in the liver, such as PEPCK, G6Pase and PC. Such assays can be cell-free assays, which include combining PGC-1 (or a biologically active portion thereof), a PGC-1 target molecule, and a candidate/test compound, under conditions wherein but for the presence of the candidate compound, PGC-1 interacts with (e.g., binds to) the target molecule, and detecting the formation of a complex or interaction/reaction between PGC-1 and its target molecule. Detection of complex formation can include direct quantitation of the complex by, for example, measuring inductive effects of the PGC-1 protein. A statistically significant change, such as a decrease, in the interaction of the PGC-1 and target molecule (e.g., in the formation of a complex between the PGC-1 and the target molecule) in the presence of a candidate compound (relative to what is detected in the absence of the candidate compound) is indicative of modulation (e.g., stimulation or inhibition) of the interaction between the PGC-1 protein and the target molecule. Modulation of the formation of complexes between the PGC-1 protein and the target molecule can be quantitated using, for example, an immunoassay.

Cell based assays employing PGC-1 expressing cells for drug screening also can be used to identify compounds that inhibit the ability of PGC-1 to induce expression of genes encoding gluconeogenic enzymes. For example, the regulatory regions associated with genes encoding the gluconeogenic enzymes can be placed upstream of a luciferase gene in a cell which also expresses PGC-1. The cell can be tested with candidate compounds and those which inhibit transcriptional activation of luciferase can be selected and further screened to verify that the inhibited transcriptional activation was in fact mediated by PGC-1.

Other cell based assays can be used to screen for drugs having an effect on the level of expression of PGC-1 protein or nucleic acid. In this case, a cell can be contacted with a candidate compound and the expression of PGC-1 mRNA or protein in the cell determined. The level of expression of PGC-1 mRNA or protein in the presence of the candidate compound is compared to the level of expression of PGC-1 mRNA or protein in the absence of the candidate compound. Candidate compounds which inhibit PGC-1 the level of mRNA through transcription or turnover can be identified.

Enabling technology for the above drug screening assays well known to the skilled artisan includes, for example, the nucleotide and amino acid sequence of PGC-1, vectors encoding PGC-1, host cells containing the vectors and methods to express the PGC-1 or portions thereof in vitro and within cells (see, e.g., U.S. Pat. No. 6,166,192 to Spiegelman et al.; see also U.S. Pat. No. 6,063,583 to Montminy for drug screening assays involving CREB and CBP). Also known are drug screening assay formats, such as methods to immobilize either PGC-1 or its target molecule to facilitate separation of complexes from uncomplexed forms of one or both of the proteins and cell based assays for measuring the ability of the compound or agent to modulate the expression of the PGC-1 nucleic acid or activity of the PGC-1.

Methods of Administration:

As used herein, "administering" refers to means for providing an appropriate inhibitor of PGC-1's ability to induce expression of gluconeogenic genes identified as described herein, to a subject, using oral, sublingual, intravenous, subcutaneous, transcutaneous, intramuscular, intracutaneous, intrathecal, epidural, intraoccular, intracranial, intrahepatic, inhalation, rectal, vaginal, and the like administration. Administration in the form of creams, lotions, tablets, capsules, pellets, dispersible powders, granules, suppositories, syrups, elixirs, lozenges, injectable solutions, sterile aqueous or non-aqueous solutions, suspensions or emulsions, patches, and the like, is also contemplated. The active compound may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

As employed herein, the phrase "an effective amount," refers to a dose sufficient to provide circulating concentrations high enough to impart a beneficial effect on the recipient thereof. The specific therapeutically effective dose level for any particular subject will depend upon a variety of factors including the disorder being treated, the severity of the disorder, the activity of the specific polypeptide or compositions used, the route of administration, the rate of clearance of the specific polypeptide or composition, the duration of treatment, the drugs used in combination or coincident with the specific polypeptide or composition, the age, body weight, sex, diet and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. Dosage levels typically fall in the range of about 0.001 up to 100 mg/kg/day; with levels in the range of about 0.05 up to 10 mg/kg/day are generally applicable.

PGC-1 Diagnostic Assay for Diabetes Mellitus:

The invention also provides an assay for determining if an individual is predisposed to diabetes or has early stage disease. The assay involves determining the level of expression of PGC-1 protein (e.g., by contacting proteins from a biological sample from the individual with an agent specific for PGC-1, and determining the amount of the agent that bound), or determining the amount of PGC-1 encoding mRNA (e.g., by hybridizing mRNA from the biological sample with a nucleic acid probe specific for PGC-1 and determining the amount of the probe that hybridized). The term "biological sample" is intended to include tissues, cells and biological fluids isolated from a subject, as well as tissues, cells and fluids present within a subject. That is, the detection method of the invention can be used to detect PGC-1 mRNA or protein in a biological sample in vitro as well as in vivo. For example, in vitro techniques for detection of PGC-1 mRNA include Northern hybridizations and in situ hybridizations. In vitro techniques for detection of PGC-1 protein include enzyme linked immunosorbent assays (ELISAs), Western blots, immunoprecipitations and immunofluorescence, and the like. Alternatively, PGC-1 protein can be detected in vivo in a subject by introducing into the subject a labeled anti-PGC-1 antibody. For example, the antibody can be labeled with a radioactive marker whose presence and location in a subject can be detected by standard imaging techniques.

Methods to quantitate the level of expression of PGC-1 protein or encoding mRNA are described in U.S. Pat. No. 6,166,192 to Spiegelman et al. The patent describes preparation of PGC-1 nucleic acid probes, PGC-1 specific polyclonal and monoclonal antibodies and fragments thereof, and methods for linking detectable moieties to the PGC-1 specific binding agents.

Detectable moieties may be any molecule (or combinations of molecules) that may be attached or otherwise associated with another molecule so that the other molecule can be detected indirectly by detecting the detectable moiety. A detectable moiety can be a radioisotope (e.g., iodine, indium, sulfur, hydrogen etc.) a dye or fluorophor (e.g., cyanine, fluorescein, rhodamine etc.), protein (e.g., avidin, antibody, etc.), enzyme (peroxidase, phosphatase, etc.), or any other agent that can be detected directly or indirectly. An enzyme is an example of a detectable moiety detected by indirect means when the result measured relates to the substrate.

A fluorescent detectable moiety can be stimulated by a light source such as a laser, with the emitted light captured by a detector. The detector can be a charge-coupled device (CCD) or a confocal microscope, which records its intensity. In the case of an array, the intensities provided by the array image can be quantified by measuring the average or integrated intensities of the spots. Interpreting the data from a microarray experiment can be assisted using special software, including, for example, Dapple, available, for example, on the world wide web at cs.washington.edu/homes/jbuhler/research/dapple/.

A detectable moiety may include more than one chemical entity such as in fluorescent resonance energy transfer (FRET). In FRET based assays, interaction between biomolecules is measured indirectly by conjugating one of a pair of carefully selected fluorescent dyes to each of the molecules of interest. The absorption spectrum of the acceptor must overlap fluorescence emission spectrum of the donor and donor and acceptor transition dipole orientations must be approximately parallel. In FRET, when these fluorescent dyes are held in close proximity (typically 10–100 Å) due to binding of the biomolecules, a unique fluorescence signal is developed that specifically confirms the proximity and thus the binding reaction. Resonance transfer results in an overall enhancement of the emission intensity (see e.g., Ju et. al. (1995) Proc. Nat. Acad. Sci. (USA) 92:4347–4351). To achieve resonance energy transfer, the first fluorescent molecule (the "donor" fluor) absorbs light and transfers it through the resonance of excited electrons to the second fluorescent molecule (the "acceptor" fluor).

A detectable moiety as used herein can include an acceptor and donor dye combination. In one approach, one of the dye pairs can be linked to the oligonucleotide-linker and the other dye pair can be linked to the oligonucleotide immobilized on the solid support. If a hairpin can be designed into the amplification primers, one can use FRET to detect hybridization as described previously (see, e.g., Ju et. al. supra (1995a); Ju, et al. (1995b), Anal Biochem. 231(1):131–40). In this alternative, resonance transfer occurs when the labeled oligonucleotide is not hybridized, but is absent when the oligonucleotide has hybridized because hybridization extends the confirmation of the oligonucleotide, physically separating the two fluors. In yet a further approach, both the donor and acceptor dyes can be linked together and attached to the DNA fragment, the oligonucleotide linker or the amplification primer. Methods to link donor and acceptor dyes to a nucleic acid have been described previously, for example, in U.S. Pat. No. 5,945,526 to Lee et al.

When hybridization is detected by FRET, the solid support need not be washed if the hybridization conditions are suitably chosen (see e.g., Tyagi et al. (1996) Nat. Biotechnol. 14:303–308). Washing steps also may be combined with FRET based hybridization, to achieve greater discrimination, if desired.

In most cases, when donor and acceptor dyes are different, FRET can be detected by the appearance of sensitized fluorescence of the acceptor or by quenching of donor fluorescence. When the donor and acceptor are the same, FRET can be detected by the resulting fluorescence. Donor/acceptor pairs of dyes that can be used include, for example, fluorescein/tetramethylrohdamine, IAEDANS/fluroescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.).

Signal amplification in the assay may be achieved using labeled dendrimers as the detectable moiety. A dendrimer is a bulky three dimensional molecule that can be labeled to high specific activity, providing signal amplification (see, e.g., Physiol Genomics 3:93–99, 2000). Fluorescently labeled dendrimers are available from Genisphere (Montvale, N.J.). These may be chemically conjugated to the DNA by methods known in the art.

Assays for protein or nucleic acid can be conducted on a solid phase such as a microarray and subject to automated analysis. For nucleic acid detection, the array may contain various nucleic acid probes immobilized to array. If protein detection is desired, the array may contain an antibody, biotin, avidin or other specific binding protein. The solid support may be flat but also may take on alternative surface configurations. For example, the solid support may contain raised or depressed regions on which oligonucleotides synthesis takes place or where oligonucleotides or protein are attached. The solid support will be chosen to provide appropriate light-absorbing characteristics. Thus, the support may be a polymerized Langmuir Blodgett film, functionalized glass, Si, Ge, GaAs, GaP, $SiO_2$, $SiN_4$, modified silicon, or any one of a variety of gels or polymers such as (poly) tetrafluoroethylene, (poly)vinylidendifluoride, polystyrene, polycarbonate, or combinations thereof. The solid support may be a glass microscope slide.

The surface of the solid support can contain reactive groups, which could be carboxyl, amino, hydroxyl, thiol, or the like suitable for conjugating to a reactive group associated with oligonucleotides or protein. Oligonucleotides or protein can be attached to the solid support by chemical or physical means such as through ionic, covalent or other forces well known in the art. Oligonucleotides or protein also can be attached to a solid support by means of a spacer molecule, essentially as described in U.S. Pat. No. 5,556,752 to Lockhart et al. A spacer molecule typically comprises between 6–50 atoms in length although larger and shorter spacers are possible and includes a surface attaching portion that attaches to the solid support.

Attachment to the support can be accomplished by carbon—carbon bonds, using supports having, for instance, (poly)trifluorochloroethylene surfaces or, preferably, by siloxane bonds, employing glass or silicon oxide as the solid support, for example. Siloxane bonding can be formed by reacting the support with trichlorosilyl or trialkoxysilyl groups of the spacer. Aminoalkylsilanes and hydroxyalkylsilanes, bis(2-hydroxyethyl)-aminopropyltriethoxysilane, 2-hydroxyethylaminopropyltriethoxysilane, aminopropyltriethoxysilane or hydroxypropyltriethoxysilane are useful are surface attaching groups. Additionally, for use in synthesis of oligonucleotides, the spacer can have a protecting group, attached to a functional group (i.e., hydroxyl, amino or carboxylic acid) on the distal or terminal end of the spacer (opposite the solid support). After deprotection and coupling, the distal end can be covalently bound to an oligomer.

Another solid support is a microelectronic chip as described, for example, in U.S. Pat. No. 6,051,380 to Sosnowski et al., No. 6,129,828 to Sheldon, III et al., and U.S. Pat. No. 6,017,696 to Heller. This type of chip exploits electronically accelerated hybridization conducted under very low salt conditions, which avoids problems, with DNA conformation and secondary structure, associated with other hybridization methods. Immobilized oligonucleotides can be moved electronically to specific sites on the microchip, and then hybridization is determined. In the electronic mediated approach, use of an electronically mediated, active hybridization process to move and concentrate target DNA molecules reduces the time to detect hybridization from hours (as in conventional, passive methodology) to minutes.

The oligonucleotides can be attached, via conventional technology, to a solid support in the form of a microarray, also known as a "DNA chip," a "DNA microarray," a "gene array," a "gene chip," and a "genome chip," or in the form of a macroarray. In this context, an array is an orderly arrangement of samples that enables the matching of known and unknown DNA samples, founded on base-pairing rules, and the automation of identifying the unknowns. A similar chip can be made for protein such as a antibody specific for PGC-1.

"Microarray" and "macroarray" are relative terms, distinguished from each other in terms of the diameter of the sample spots involved. Thus, microarray sample spots typically are about 200 microns in diameter or less, making it possible to array thousands of sample spots on a single chip. These arrays can be prepared by hand but, preferably, are made using specialized robotics and read by means of specialized imaging equipment, particularly with spots with diameters in the lower-end range. By contrast, macroarray sample spots typically are greater than 200 microns in diameter, making them suitable for imaging by gel and blot scanners. Macroarrays may be prepared by hand using standard microplates or standard blotting membranes.

A microarray containing immobilized oligonucleotides can be prepared by a number of well-known approaches including, for example, light-directed methods, such as VLSIPS™ (see U.S. Pat. No. 5,143,854), mechanical methods such as described in PCT No. 92/10183 or U.S. Pat. No. 5,384,261, bead-based methods described, for example, in PCT US/93/04145, and pin-based methods as detailed in U.S. Pat. No. 5,288,514, inter alia. U.S. Pat. No. 5,556,752 to Lockhart describes the preparation of a library of different, double-stranded oligonucleotides as a microarray, using the VLSIPS,™ and this approach also is suitable for preparing a library of oligonucleotides in a microarray. Flow channel techniques, as described U.S. Pat. No. 5,677,195 and No. 5,384,261, also can be employed to prepare a microarray chip that has a variety of different immobilized oligonucleotides. In this case, certain activated regions of the substrate are mechanically separated from other regions when the oligonucleotides are delivered through a flow channel to the support. As noted, the Lockhart '752 patent describes flow channel methodology in some detail, including the use of protective coating-wetting facilitators to enhance the directed channeling of liquids though designated flow paths.

Spotting methods also can be used to prepare a microarray biochip with a variety of oligonucleotides or protein. In this case, reactants are delivered by directly depositing relatively small quantities in selected regions of the support. In some steps, of course, the entire support surface can be sprayed or otherwise coated with a particular solution. In particular formats, a dispenser moves from region to region, depositing only as much oligonucleotides, protein or other reagent as necessary at each stop. Typical dispensers include a micropipette, nanopipette, ink-jet type cartridge or pin to deliver the oligonucleotide or protein containing solution or other fluid to the support and, optionally, a robotic system to control the position of these delivery devices with respect to the support. In other formats, the dispenser includes a series of tubes or multiple well trays, a manifold, and an array of delivery devices so that various reagents can be delivered to the reaction regions simultaneously.

Spotting methods are well known and include, for example, those described in U.S. Pat. No. 5,288,514, No. 5,312,233 and No. 6,024,138. In some cases, a combination of flowing channel and "spotting" on predefined regions of the support also can be used to prepare microarray biochips with immobilized oligonucleotides or protein.

Information and examples of constructing microarrays are readily available in the art, such as in Cheung et al., *Nature Genetics Supplement*, Vol. 21, pp. 15–19 (1999); Lipshutz et al., *Nature Genetics Supplement*, Vol. 21, pp. 20–24 (1999); Brown & Botstein, *Nature Genetics Supplement*, Vol. 21, pp. 33–37 (1999); Shoemaker et al., *Nature*, Vol. 409, pp. 922–27 (2001); Schena et al., Science (1995) 467–470; Schena et al., P.N.A.S. U.S.A. (1996) 93: 10614–10616; Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Numerous patents related to microarray development include U.S. Pat. Nos. 5,082,830; 6,110,426; 6,004,755, 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, and 5,700,637 and WO 97/27317.

Detection of PGC-1 encoding mRNA levels also may include use of amplification techniques such as the reverse transcriptase in conjunction with polymerase chain reaction (RTPCR). PCR synthesis of DNA fragments occurs by repeated cycles of heat denaturation of DNA fragments (i.e. heating to at least about 95° C.), incubation at a temperature permitting hybridization of amplification primers to template DNA, and primer extension. These cycles can be performed manually or, preferably, automatically. Thermal cyclers such as the Perkin-Elmer Cetus® cycler (Perkin-Elmer Corp., Boston, Mass.) are specifically designed for automating the PCR process and are preferred. The number of cycles per round of synthesis generally varies from 2 to more than 50, the optimum number being readily determined by considering the source and amount of the nucleic acid template, the desired yield, and the procedure to be used for detection of the DNA. Heat stable amplification enzymes such as pwo, *Thermus aquaticus* or *Thermococcus litoralis* DNA polymerases are commercially available and eliminate the need to add enzyme after each denaturation cycle. Basic PCR techniques are described in U.S. patents by Saiki et al. (1988 Science 239:487–491) and by U.S. Pat. Nos. 4,683,195, 4,683,202 and 4,800,159. Other variations of PCR that are applicable herein are well known in the art.

The invention will now be described in greater detail by reference to the following non-limiting examples.

EXAMPLES

Example I

Regulation of Gluconeogenesis by CREB and PGC-1

Recombinant adenoviruses. Adenoviruses expressing either ACREB or PGC-1 were generated through homologous recombination between a linearized transfer vector pAD-Track and the adenoviral backbone vector pAD-Easy as described[21]. pAD-ACREB contained a NotI/SpeI fragment from ZEO-ACREB encoding a Flag-tagged ACREB polypeptide[22]. pAD-PGC-1 carried the entire murine PGC-1 cDNA encoding all but the c-terminal four amino acids. Both viruses co-expressed the green fluorescent protein (GFP) transcribed from a second independent CMV promoter to monitor viral infection efficiency. Adenovirus coding for GFP only (pAD-GFP) was used as a control in all experiments. Viruses were purified by the CsCl method and dialyzed against PBS buffer containing 10% glycerol prior to animal injections as described[23].

Animal experiments. Male 6-week old C57B16 or db/db mice were obtained from The Jackson Laboratory (Bar Harbor, Me., USA) and maintained on a 12-hour light-dark cycle with regular unrestricted diet. For virus injections, animals were anaesthetized with Iso-Flurane and a total of $1\times10^9$ plaque-forming units per recombinant virus was administered via systemic tail vein injection. In each experiment at least six animals received identical treatments. Animals were fasted for 9–18h overnight with free access to water. Blood glucose was monitored at the end of each fasting period for at least 8 consecutive days. Blood glucose was also measured in the non-fasted state immediately before food withdrawal. Blood samples were collected from the tail vein. Liver tissue for RNA and protein isolation was immediately frozen in liquid nitrogen. Additional liver samples were fixed in 10% formaldehyde, sectioned with a cryomicrotome, and investigated for viral infection efficiency by fluorescence microscopy. Studies with CREB knock out mice carrying a targeted disruption of the CREB DNA binding domain and leucine zipper region[15] were performed as described above.

Blood metabolites. Blood glucose values were determined from whole blood using an automatic glucose monitor (One Touch, Lifescan). Plasma insulin levels were determined using a commercial insulin ELISA kit (Crystal Chem. Inc., Chicago).

Quantitative Taqman RT-PCR and Northern blot Analysis. Poly(A)+ RNA and total RNA were extracted from homogenized mice livers using the Fast Track 2.0™ (Invitrogen, Carlsbad) or the RNeasy (Qiagen, Valencia) kit. RNA samples were treated with DNase I (Promega) and RNA quality was assessed by gel electrophoresis. cDNA was prepared by reverse transcription of 250 ng mRNA or 500 ng total RNA using the Superscript II enzyme and Oligo dT primer (GIBCO BRL, Grand Island). The resulting cDNAs were amplified using the SYBR green PCR kit and a ABIPRISM 7700 Sequence detector (Perkin Elmer, Foster City). All RNA expression data from the TaqMan analysis was normalized to GAPDH expression in the corresponding sample. Northern blot assays were performed as previously described[22].

Protein analysis. Protein was extracted from frozen liver samples in SDS-Urea-lysis buffer and 20 μg of protein were loaded onto a 12% SDS-polyacrylamide gel and blotted onto nitrocellulose membrane. Western blot assays were performed as previously described[22].

Plasmids. Expression plasmids pZEO-ACREB[22] and pcDNA3-PGC-1[24] have been described previously. Liver specific A-CREB transgene was constructed by inserting A-CREB cDNA into a liver specific albumin promoter/enhancer plasmid[5]. To construct luciferase expression plasmids –490PEPCKLuc and –355PEPCKLuc BamHI/BglII fragments of the PEPCK promoter region containing 490 or 355 bp of the mouse PEPCK 5'-flanking region, respectively, were cloned into the pGL3 basic luciferase reporter vector (Promega, St. Luis Obispo). PGC-1 reporter mPGCLuc was constructed by inserting a 230 bp fragment of the mouse PGC-1 promoter containing 170 bp of the 5'-flanking region and 68 bp of Exon 1 into the pGL3 vector.

Cell culture and transient transfection assays. Human hepatoma HepG2 cells were transfected using the Lipofectamine 2000 reagent (GIBCO BRL) according to manufacturers instructions (500 ng of indicator plasmid/well). Where indicated, expression plasmids encoding A-CREB (pZeo-ACREB)[22] or PGC-1 (pcDNA3-PGC-1)[24] were cotransfected (50 ng or 800 ng plasmid/well, respectively). Cotransfections were performed with a constant DNA amount by adding the empty pcDNA3 vector (Invitrogen). Cells were treated with Forskolin (10 μM) and/or Dexamethasone (100 nM) or insulin (10 nM) for 14 h. Cell extracts were prepared 48 h after transfection and the luciferase assay was performed as described previously[25], normalizing to activity from cotransfected Rous sarcoma virus-β-galactosidase expression plasmid (100 ng plasmid/well).

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

References referred to herein by footnote are as follows:
1. Yoon, et al *Nature*, submitted (2001).
2. Gonzalez, G. A. & Montminy, M. R. Cyclic AMP stimulates somatostatin gene transcription by phosphorylation of CREB at Serine 133. *Cell* 59, 675–680 (1989).
3. Liu, J. S., Park, E. A., Gurney, A. L., Roesler, W. J. & Hanson, R. W. Cyclic AMP induction of phosphoenolpyruvate carboxykinase (GTP) gene transcription is mediated by multiple promoter elements. *J Biol Chem* 266, 19095–19102. (1991).
4. Quinn, P. G. & Granner, D. K. Cyclic AMP-dependent protein kinase regulates transcription of the phosphoenolpyruvate carboxykinase gene but not binding of nuclear factors to the cyclic AMP regulatory element. *Mol Cell Biol* 10, 3357–3364. (1990).
5. Liu, J. K., Bergman, Y. & Zaret, K. S. The mouse albumin promoter and a distal upstream site are simultaneously DNase I hypersensitive in liver chromatin and bind similar liver-abundant factors in vitro. *Genes Dev* 2, 528–541. (1988).
6. Ahn, S. et al. A dominant negative inhibitor of CREB reveals that it is a general mediator stimulus-dependent transcription of c-fos. *Molec. Cell. Biol.* 18, 967–977 (1998).
7. Long, F., Schipani, E., Asahara, H., Kronenberg, H. & Montminy, M. The CREB family of activators is required for endochondral bone development. *Development* 128, 541–550.
8. Consoli, A. Role of liver in pathophysiology of NIDDM. *Diabetes Care* 15, 430–441. (1992).
9. Lee, G. H. et al. Abnormal splicing of the leptin receptor in diabetic mice. *Nature* 379, 632–635. (1996).
10. Chen, H. et al. Evidence that the diabetes gene encodes the leptin receptor: identification of a mutation in the leptin receptor gene in db/db mice. *Cell* 84, 491–495. (1996).
11. Wexler, I. D. et al. Molecular characterization of pyruvate carboxylase deficiency in two consanguineous families. *Pediatr Res* 43, 579–584. (1998).
12. Lei, K. J. et al. Glucose-6-phosphatase dependent substrate transport in the glycogen storage disease type-1a mouse. *Nat Genet* 13, 203–209. (1996).
13. Schmoll, D. et al. Identification of a cAMP response element within the glucose-6-phosphatase hydrolytic subunit gene promoter which is involved in the transcriptional regulation by cAMP and glucocorticoids in H4IIE hepatoma cells. *Biochem J* 338, 457–463. (1999).
14. Jitrapakdee, S., Booker, G. W., Cassady, A. I. & Wallace, J. C. The rat pyruvate carboxylase gene structure. Alternate promoters generate multiple transcripts with the 5'-end heterogeneity. *J Biol Chem* 272, 20522–20530. (1997).
15. Rudolph, D. et al. Impaired fetal T cell development and perinatal lethality in mice lacking the cAMP response element binding protein. *Proc Natl Acad Sci USA* 95, 4481–4486 (1998).
16. Short, J. M., Wynshaw-Boris, A., Short, H. P. & Hanson, R. W. Characterization of the phosphoenolpyruvate carboxykinase (GTP) promoter-regulatory region. II. Identification of cAMP and glucocorticoid regulatory domains. *J Biol Chem* 261, 9721–9726 (1986).
17. Wang, J. C., Stromstedt, P. E., Sugiyama, T. & Granner, D. K. The phosphoenolpyruvate carboxykinase gene glucocorticoid response unit: identification of the functional domains of accessory factors HNF3 beta (hepatic nuclear factor-3 beta) and HNF4 and the necessity of proper alignment of their cognate binding sites. *Mol Endocrinol* 13, 604–618. (1999).
18. Imai, E. et al. Characterization of a complex glucocorticoid response unit in the phosphoenolpyruvate carboxykinase gene. *Mol Cell Biol* 10, 4712-4719. (1990).
19. Friedman, J. E. et al. Phosphoenolpyruvate carboxykinase (GTP) gene transcription and hyperglycemia are regulated by glucocorticoids in genetically obese db/db transgenic mice. *J Biol Chem* 272, 31475–31481. (1997).
20. Knutti, D., Kaul, A. & Kralli, A. A tissue-specific coactivator of steroid receptors, identified in a functional genetic screen. *Mol Cell Biol* 20, 2411–2422. (2000).
21. He, T. et al. A simplified system for generating recombinant adenoviruses. *Proc. Natl. Acad. Sci.* 95, 2509–2514 (1998).
22. Michael, L. F., Asahara, H., Shulman, A., Kraus, W. & Montminy, M. The phosphorylation status of a cyclic AMP-responsive activator is modulated via a chromatin-dependent mechanism. *Mol Cell Biol.* 20, 1596–1603 (2000).
23. Becker, T. et al. Use of recombinant adenovirus for metabolic engineering of mammalian cells. *Methods Cell Biol,* 161–189 (1994).
24. Puigserver, P. et al. A cold-inducible coactivator of nuclear receptors linked to adaptive thermogenesis. *Cell* 92, 829–839 (1998).
25. Nakajima, T. et al. RNA Helicase A mediates association of CBP with RNA polymerase II. *Cell* 90, 1107–1112 (1997).

That which is claimed is:

1. An in vitro method of identifying a compound that modulates gluconeogenesis, said method comprising:
   contacting CREB and a nucleic acid comprising a PGC-1 promoter with a test compound, and
   determining if the test compound modulates binding between CREB and the PGC-1 promoter,
   wherein said PGC-1 promoter comprises position minus 116 to minus 133 of the human PGC-1 gene.

2. The method of claim 1 wherein said test compound is the dominant negative mutant of CREB, A-CREB.

3. The method of claim 1 wherein said test compound reduces binding between CREB and said PGC-1 promoter.

* * * * *